United States Patent
Bhagavat et al.

(10) Patent No.: US 9,883,822 B2
(45) Date of Patent: *Feb. 6, 2018

(54) BIOMETRIC SENSOR CHIP HAVING DISTRIBUTED SENSOR AND CONTROL CIRCUITRY

(71) Applicant: Apple Inc., Cupertino, CA (US)

(72) Inventors: Milind S. Bhagavat, Cupertino, CA (US); Jun Zhai, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/181,229

(22) Filed: Jun. 13, 2016

(65) Prior Publication Data

US 2016/0278671 A1  Sep. 29, 2016

Related U.S. Application Data

(63) Continuation-in-part of application No. 15/090,474, filed on Apr. 4, 2016, now abandoned, which is a
(Continued)

(51) Int. Cl.
*G06K 9/00* (2006.01)
*A61B 5/117* (2016.01)
(Continued)

(52) U.S. Cl.
CPC ............ *A61B 5/1172* (2013.01); *A61B 5/053* (2013.01); *G06K 9/0002* (2013.01);
(Continued)

(58) Field of Classification Search
CPC ............ G06K 9/00013; G06K 9/0002; G06K 9/00053; G06K 9/209; G06F 3/041;
(Continued)

(56) References Cited

U.S. PATENT DOCUMENTS

| 3,876,942 A | 4/1975 | Koster et al. ................. 325/115 |
| 4,421,418 A | 12/1983 | Morishima ..................... 368/69 |

(Continued)

FOREIGN PATENT DOCUMENTS

| AU | 2013100571 A4 | 5/2013 | ............... G06F 3/02 |
| CN | 1164075 A | 11/1997 | ............... G06K 9/00 |

(Continued)

OTHER PUBLICATIONS

Author Unknown, "DC-to-DC converter," Wikipedia, the free encyclopedia, Apr. 12, 2012, XP 055092945, retrieved from the internet on Dec. 11, 2013: URL:http://en.wikipedia.org/w/index.php?title=DC-to-DC_converter&oldid=487061873.

(Continued)

*Primary Examiner* — Andrew W Johns
(74) *Attorney, Agent, or Firm* — Brownstein Hyatt Farber Schreck, LLP

(57) ABSTRACT

A sensor includes a sensor array formed on a first side of a substrate and at least one circuit operative to communicate with the sensor array formed on a second side of the substrate. At least one via extends through the substrate to electrically connect the sensor array to the at least one circuit. Placing the at least one circuit on the second side of the substrate allows the sensor array to occupy substantially all of the first side of the substrate.

16 Claims, 9 Drawing Sheets

Related U.S. Application Data continuation of application No. 14/294,903, filed on Jun. 3, 2014, now Pat. No. 9,305,959.

(60) Provisional application No. 61/831,586, filed on Jun. 5, 2013.

(51) Int. Cl.
*A61B 5/1172* (2016.01)
*A61B 5/053* (2006.01)
*H01L 27/146* (2006.01)

(52) U.S. Cl.
CPC .. *H01L 27/14634* (2013.01); *H01L 27/14636* (2013.01); *A61B 2562/0214* (2013.01); *A61B 2562/182* (2013.01)

(58) Field of Classification Search
CPC . G06F 3/044; G06F 2203/04103; G01D 5/24; G01R 27/2605; G02F 1/13338; H01L 23/52; H01L 23/535; H01L 23/5384
See application file for complete search history.

(56) References Cited

U.S. PATENT DOCUMENTS

| | | | |
|---|---|---|---|
| 5,650,597 A | 7/1997 | Redmayne | 178/19 |
| 5,731,222 A | 3/1998 | Malloy et al. | 437/182 |
| 5,953,441 A | 9/1999 | Setlak | 382/132 |
| 5,963,679 A | 10/1999 | Setlak | 382/124 |
| 6,011,859 A * | 1/2000 | Kalnitsky et al. | 382/124 |
| 6,049,620 A | 4/2000 | Dickinson et al. | 382/124 |
| 6,067,368 A | 5/2000 | Setlak et al. | 382/124 |
| 6,088,471 A | 7/2000 | Setlak et al. | 382/124 |
| 6,259,804 B1 | 7/2001 | Setlak et al. | 382/124 |
| 6,327,376 B1 | 12/2001 | Harkin | 382/124 |
| 6,400,359 B1 | 6/2002 | Katabami | 345/173 |
| 6,483,931 B2 | 11/2002 | Kalnitsky et al. | 382/124 |
| 6,522,773 B1 | 2/2003 | Houdeau | 382/124 |
| 6,628,812 B1 | 9/2003 | Setlak et al. | 382/124 |
| 6,647,133 B1 | 11/2003 | Morita | 382/124 |
| 6,734,655 B1 | 5/2004 | Javanifard et al. | 323/222 |
| 6,737,329 B2 | 5/2004 | Lepert et al. | 438/393 |
| 6,815,657 B2 | 11/2004 | Toyoshima et al. | 250/214 R |
| 6,882,338 B2 | 4/2005 | Flowers | 345/174 |
| 6,906,529 B2 | 6/2005 | Blanchard | 324/662 |
| 6,914,517 B2 | 7/2005 | Kinsella | 340/5.83 |
| 6,996,492 B1 | 2/2006 | Testoni | 702/134 |
| 7,042,317 B2 | 5/2006 | Xiao et al. | 333/214 |
| 7,043,060 B2 | 5/2006 | Quintana | 382/124 |
| 7,194,113 B2 | 3/2007 | Greschitz et al. | 382/124 |
| 7,202,764 B2 | 4/2007 | Deligianni et al. | 335/78 |
| 7,227,213 B2 | 6/2007 | Mastromatteo et al. | 257/304 |
| 7,236,765 B2 | 6/2007 | Bonicatto et al. | 455/402 |
| 7,251,351 B2 | 7/2007 | Mathiassen et al. | 382/124 |
| 7,262,609 B2 | 8/2007 | Reynolds | 324/678 |
| 7,290,323 B2 | 11/2007 | Deconde et al. | 29/595 |
| 7,318,550 B2 | 1/2008 | Bonalle et al. | 235/380 |
| 7,397,096 B2 | 7/2008 | Chou et al. | 257/414 |
| 7,403,749 B2 | 7/2008 | Kuijstermans et al. | 455/114.2 |
| 7,460,109 B2 | 12/2008 | Safai et al. | 345/173 |
| 7,521,942 B2 | 4/2009 | Reynolds | 324/688 |
| 7,536,039 B2 | 5/2009 | Shinoda et al. | 382/124 |
| 7,548,636 B2 | 6/2009 | Shimamura et al. | 382/115 |
| 7,583,092 B2 | 9/2009 | Reynolds et al. | 324/688 |
| 7,627,151 B2 | 12/2009 | Rowe | 382/124 |
| 7,675,388 B2 | 3/2010 | Cardona et al. | 333/133 |
| 7,683,638 B2 | 3/2010 | Chuang et al. | 324/686 |
| 7,696,497 B2 | 4/2010 | Rogers | 250/492.22 |
| 7,777,501 B2 | 8/2010 | Reynolds et al. | 324/678 |
| 7,835,553 B2 | 11/2010 | Miyasaka | 382/124 |
| 7,902,474 B2 | 3/2011 | Mittleman et al. | 200/516 |
| 7,986,153 B2 | 7/2011 | Easter | 324/678 |
| 8,031,916 B2 | 10/2011 | Abiko et al. | 382/126 |
| 8,041,083 B2 | 10/2011 | Pai et al. | 382/124 |
| 8,070,695 B2 | 12/2011 | Gupta et al. | 600/594 |
| 8,073,204 B2 | 12/2011 | Kramer et al. | 382/115 |
| 8,093,099 B2 | 1/2012 | Purushothaman et al. | 438/107 |
| 8,107,212 B2 | 1/2012 | Nelson et al. | 361/220 |
| 8,111,136 B2 | 2/2012 | Wong et al. | 340/5.83 |
| 8,116,540 B2 | 2/2012 | Dean et al. | 382/124 |
| 8,174,372 B2 | 5/2012 | da Costa | 340/407.2 |
| 8,195,117 B2 | 6/2012 | Bult et al. | 455/234.1 |
| 8,196,809 B2 | 6/2012 | Thorstensson | 235/375 |
| 8,243,030 B2 | 8/2012 | Jiang et al. | 345/173 |
| 8,264,463 B2 | 9/2012 | Takashima et al. | 345/169 |
| 8,283,934 B2 | 10/2012 | Nishizono | 324/658 |
| 8,305,360 B2 | 11/2012 | Wu | 345/174 |
| 8,358,816 B2 | 1/2013 | Sherlock et al. | 382/124 |
| 8,362,488 B2 | 1/2013 | Chaug et al. | 257/72 |
| 8,366,633 B2 | 2/2013 | Wolf | 600/561 |
| 8,456,330 B2 | 6/2013 | Filson et al. | 341/33 |
| 8,461,948 B2 | 6/2013 | Pulskamp et al. | 335/78 |
| 8,482,381 B2 | 7/2013 | Chatterjee et al. | 340/5.52 |
| 8,482,546 B2 | 7/2013 | Chai et al. | 345/174 |
| 8,529,474 B2 | 9/2013 | Gupta et al. | 600/594 |
| 8,598,555 B2 | 12/2013 | Guerrero et al. | 250/556 |
| 8,606,227 B2 | 12/2013 | Karam et al. | 455/410 |
| 8,633,916 B2 | 1/2014 | Bernstein et al. | 345/174 |
| 8,716,613 B2 | 5/2014 | Perezselsky et al. | 178/18.03 |
| 8,717,775 B1 | 5/2014 | Bolognia et al. | 361/803 |
| 8,723,062 B2 | 5/2014 | Chen et al. | 200/314 |
| 8,724,038 B2 | 5/2014 | Ganapathi et al. | 349/12 |
| 8,736,001 B2 | 5/2014 | Salatino et al. | 257/415 |
| 8,743,082 B2 | 6/2014 | Ganapathi et al. | 345/174 |
| 8,743,083 B2 | 6/2014 | Zanone et al. | 345/174 |
| 8,748,842 B2 | 6/2014 | Ohashi | 250/396 R |
| 8,749,523 B2 | 6/2014 | Pance et al. | 345/175 |
| 8,779,540 B2 | 7/2014 | Kerness et al. | 257/432 |
| 8,780,071 B2 | 7/2014 | Chen et al. | 345/174 |
| 8,782,775 B2 | 7/2014 | Fadell et al. | 726/16 |
| 8,791,792 B2 | 7/2014 | Benkley, III | G06K 9/0002 |
| 8,797,298 B2 | 8/2014 | Brosnan et al. | G06F 3/042 |
| 8,841,749 B2 | 9/2014 | Joblot et al. | B01L 23/481 |
| 8,860,683 B2 | 10/2014 | Baumbach | G06F 3/044 |
| 8,866,347 B2 | 10/2014 | Benkley, III | 307/116 |
| 8,888,004 B2 | 11/2014 | Setlak et al. | G06K 9/0002 |
| 8,890,016 B2 | 11/2014 | Silverman | H01H 13/14 |
| 8,907,897 B2 | 12/2014 | Ferren et al. | G06F 3/044 |
| 9,001,040 B2 | 4/2015 | Dean et al. | G06F 3/03547 |
| 9,001,081 B2 | 4/2015 | Pope et al. | G06K 9/0002 |
| 9,030,440 B2 | 5/2015 | Pope et al. | G06K 9/0002 |
| 9,035,895 B2 | 5/2015 | Bussat et al. | G06F 3/0418 |
| 9,065,321 B2 | 6/2015 | Divan et al. | H02M 1/00 |
| 9,099,282 B2 | 8/2015 | Rogers et al. | H01J 37/261 |
| 9,110,538 B2 | 8/2015 | Dunko et al. | G06F 3/042 |
| 9,122,356 B2 | 9/2015 | Ozias et al. | G06F 3/044 |
| 9,135,495 B1 | 9/2015 | Pope et al. | G06K 9/00073 |
| 9,153,490 B2 | 10/2015 | Mitsuhashi et al. | H01L 21/76898 |
| 9,158,140 B2 | 10/2015 | Inoue et al. | G02F 1/1309 |
| 9,158,403 B2 | 10/2015 | Kasamatsu | G06F 3/041 |
| 9,158,958 B2 | 10/2015 | Wickboldt et al. | G06K 9/00026 |
| 9,236,412 B2 | 1/2016 | Okamoto | H01L 27/14636 |
| 9,239,655 B2 | 1/2016 | Hershman | G06F 3/004 |
| 9,268,989 B2 | 2/2016 | Pope et al. | G06K 9/0002 |
| 9,274,553 B2 | 3/2016 | Erhart et al. | G06F 1/1626 |
| 9,305,959 B2 | 4/2016 | Bhagavat et al. | H01L 27/14636 |
| 9,316,677 B2 | 4/2016 | Grunthaner et al. | G01R 31/021 |
| 9,323,393 B2 | 4/2016 | Djordjev et al. | G06F 3/0421 |
| 9,323,972 B2 | 4/2016 | Bussat et al. | G06K 9/00013 |
| 9,460,332 B1 | 10/2016 | Bussat | G06K 9/0002 |
| 9,551,783 B2 | 1/2017 | Schneider et al. | G01S 7/56 |
| 2002/0065054 A1 | 5/2002 | Humphreys et al. | 455/90 |
| 2005/0156906 A1 | 7/2005 | Chiu | 345/173 |
| 2007/0076923 A1 | 4/2007 | Chiu | 382/124 |
| 2008/0025582 A1 | 1/2008 | Kobayashi | 382/124 |
| 2008/0049980 A1 | 2/2008 | Castaneda et al. | 382/115 |
| 2008/0238878 A1 | 10/2008 | Wang | 345/173 |
| 2009/0008729 A1 | 1/2009 | Yang et al. | 257/432 |
| 2009/0085879 A1 | 4/2009 | Dai et al. | 345/173 |
| 2009/0260900 A1 | 10/2009 | Ure | 178/19.03 |

(56) References Cited

U.S. PATENT DOCUMENTS

| | | | |
|---|---|---|---|
| 2010/0110019 A1 | 5/2010 | Ozias et al. | 345/173 |
| 2010/0156595 A1 | 6/2010 | Wong et al. | 340/5.53 |
| 2010/0176271 A1 | 7/2010 | Rim et al. | 250/208.1 |
| 2010/0201485 A1 | 8/2010 | Chou | 340/5.83 |
| 2010/0321159 A1 | 12/2010 | Stewart | 340/5.83 |
| 2011/0102569 A1 | 5/2011 | Erhart | 348/77 |
| 2011/0122082 A1 | 5/2011 | Orellana | 345/173 |
| 2011/0234623 A1 | 9/2011 | Ure | 345/592 |
| 2011/0267298 A1 | 11/2011 | Erhart et al. | 345/173 |
| 2011/0298711 A1 | 12/2011 | Dean et al. | 345/161 |
| 2012/0090757 A1 | 4/2012 | Buchan et al. | 156/60 |
| 2012/0097510 A1 | 4/2012 | Mitchell | 200/333 |
| 2012/0113044 A1 | 5/2012 | Strazisar et al. | 345/174 |
| 2012/0206406 A1 | 8/2012 | Kim et al. | 345/174 |
| 2012/0242635 A1 | 9/2012 | Erhart et al. | 345/207 |
| 2012/0267740 A1 | 10/2012 | Okamoto | 257/432 |
| 2012/0287587 A1 | 11/2012 | Los | 361/749 |
| 2013/0015868 A1 | 1/2013 | Peng | 324/688 |
| 2013/0141388 A1 | 6/2013 | Ludwig et al. | 345/174 |
| 2013/0194071 A1 | 8/2013 | Slogedal | G06K 9/0002 |
| 2013/0231046 A1 | 9/2013 | Pope et al. | 455/41.1 |
| 2013/0271422 A1 | 10/2013 | Hotelling et al. | G06F 3/044 |
| 2013/0279769 A1 | 10/2013 | Benkley, III et al. | G06K 9/00013 |
| 2013/0307818 A1 | 11/2013 | Pope et al. | 345/174 |
| 2014/0103943 A1 | 4/2014 | Dunlap et al. | 324/663 |
| 2014/0135597 A1 | 5/2014 | Wolf, II | |
| 2014/0216914 A1 | 8/2014 | Pope et al. | 200/600 |
| 2014/0218339 A1 | 8/2014 | Hotelling et al. | 345/174 |
| 2014/0241595 A1 | 8/2014 | Bernstein et al. | G06K 9/00013 |
| 2014/0361395 A1 | 12/2014 | Bhagavat et al. | H01L 27/14636 |
| 2015/0002459 A1 | 1/2015 | Watanabe et al. | G06F 3/044 |
| 2015/0022495 A1 | 1/2015 | Bussat et al. | G06F 3/041 |
| 2015/0036065 A1 | 2/2015 | Yousefpor et al. | G06K 9/0002 |
| 2015/0070079 A1 | 3/2015 | Yang et al. | H03K 17/9622 |
| 2015/0071509 A1 | 3/2015 | Myers | G06K 9/00 |
| 2015/0248574 A1 | 9/2015 | Mrazek et al. | G06K 9/00033 |
| 2016/0070383 A1 | 3/2016 | Toyoshima et al. | G06F 3/044 |
| 2016/0092714 A1 | 3/2016 | Yazdandoost et al. | G06K 9/0002 |
| 2016/0092715 A1 | 3/2016 | Yazdandoost et al. | G06K 9/0002 |
| 2016/0092716 A1 | 3/2016 | Yazdandoost et al. | G06K 9/0002 |
| 2016/0217311 A1 | 7/2016 | Bhagavat et al. | G06K 9/0002 |
| 2016/0267313 A1 | 9/2016 | Pope et al. | G06K 9/0002 |
| 2017/0109565 A1 | 4/2017 | Pope et al. | G06K 9/00087 |
| 2017/0351902 A1 | 12/2017 | Pope et al. | G06K 9/00087 |

FOREIGN PATENT DOCUMENTS

| | | | | |
|---|---|---|---|---|
| CN | 1164076 A | 11/1997 | | G06K 9/00 |
| CN | 1172308 A | 2/1998 | | G06K 9/00 |
| CN | 1278347 A | 12/2000 | | G06K 9/20 |
| CN | 1450489 A | 10/2003 | | G06K 9/62 |
| CN | 1463409 A | 12/2003 | | G06K 9/20 |
| CN | 1538142 A | 10/2004 | | G01B 7/28 |
| CN | 1680818 A | 10/2005 | | G01R 27/26 |
| CN | 1802882 A | 7/2006 | | H05K 1/18 |
| CN | 101281589 A | 10/2008 | | G06K 9/00 |
| CN | 101339951 A | 1/2009 | | H01L 27/146 |
| CN | 101809581 A | 8/2010 | | G06F 21/20 |
| CN | 101901092 A | 12/2010 | | G06F 1/16 |
| CN | 202153359 U | 2/2012 | | G06K 9/00 |
| CN | 203535651 U | 4/2014 | | G06K 9/00 |
| EP | 0457398 A2 | 11/1991 | | G11C 27/02 |
| EP | 0791899 A2 | 8/1997 | | G07C 9/00 |
| EP | 0924656 A2 | 6/1999 | | G07C 9/00 |
| EP | 1775674 A1 | 4/2007 | | G06K 9/20 |
| JP | 2000187420 A | 4/2000 | | G03G 21/04 |
| JP | 2001339057 A | 12/2001 | | H01L 27/146 |
| JP | 2001344605 A | 12/2001 | | G06T 7/00 |
| JP | 2002502518 A | 1/2002 | | G06T 1/00 |
| JP | 2003298753 A | 10/2003 | | H04M 9/00 |
| JP | 2004310574 A | 11/2004 | | G06T 1/00 |
| JP | 2005011672 A | 1/2005 | | H01H 13/02 |
| JP | 2005115513 A | 4/2005 | | G06T 1/00 |
| JP | 2005338918 A | 12/2005 | | G06F 3/023 |
| JP | 2006134144 A | 5/2006 | | G06T 1/00 |
| JP | 3138518 U | 12/2007 | | G06T 1/00 |
| JP | 2012083829 A | 4/2012 | | G06F 21/20 |
| KR | 10-20080035133 A | 4/2008 | | H04B 1/40 |
| TW | M327066 U | 2/2008 | | G06K 9/00 |
| TW | 200937306 A | 9/2009 | | G06F 3/044 |
| TW | 201017554 A | 5/2010 | | G06K 9/00 |
| TW | 201017555 A1 | 5/2010 | | G06K 9/00 |
| TW | 201229852 A1 | 7/2012 | | G06F 3/041 |
| TW | 201346779 A | 11/2013 | | G06K 9/24 |
| WO | WO 98/052145 A1 | 11/1998 | | G06K 9/20 |
| WO | WO 01/029795 A1 | 4/2001 | | G08B 3/00 |
| WO | WO 01/059558 A1 | 8/2001 | | |
| WO | WO 04/077340 A1 | 10/2004 | | G06K 9/00 |
| WO | WO 04/098083 A1 | 11/2004 | | H04B 1/40 |
| WO | WO 05/124659 A1 | 12/2005 | | G06K 9/00 |
| WO | WO 13/130396 A2 | 9/2013 | | G06K 9/00 |
| WO | WO 14/128249 A1 | 8/2014 | | G06K 9/00 |

OTHER PUBLICATIONS

Motorola User Guide, Motorola Atrix™ 4G (MB860), Manual No. 68XXXXX468-A, Motorola Mobility Inc., 2011, 90 pages.
Motorola Atrix (MB860), Manual No. 68014798001-B, Motorola Mobility Argentina S.A., 2011, 68 pages.
Setlak, Chapter 2: Advances in Fingerprint Sensors Using RF Imaging Techniques, *Automatic Fingerprint Recognition Systems*, Editor: Ratha et al., 2003, New York, Springer Verlag, US, pp. 27-53, XP002347781, ISBN: 978-0-387-95593-3.
U.S. Appl. No. 13/842,635, filed Mar. 15, 2013, Hotelling et al.
U.S. Appl. No. 13/842,920, filed Mar. 15, 2013, Pope et al.
U.S. Appl. No. 14/022,058, filed Sep. 9, 2013, Yang et al.
U.S. Appl. No. 14/247,419, filed Apr. 8, 2014, Pope et al.
U.S. Appl. No. 14/251,304, filed Apr. 11, 2014, Hotelling et al.
U.S. Appl. No. 14/256,888, filed Apr. 18, 2014, Myers.
U.S. Appl. No. 14/294,903, filed Jun. 3, 2014, Bhagavat et al.
U.S. Appl. No. 14/335,553, filed Jul. 18, 2014, Bussat et al.
U.S. Appl. No. 14/451,076, filed Aug. 4, 2014, Yousefpor et al.
U.S. Appl. No. 14/481,568, filed Sep. 9, 2014, Bussat.
U.S. Appl. No. 14/709,388, filed May 11, 2015, Pope et al.
U.S. Appl. No. 14/855,123, filed Sep. 15, 2015, Pope et al.
U.S. Appl. No. 15/018,617, filed Feb. 8, 2016, Pope et al.
U.S. Appl. No. 15/393,610, filed Dec. 29, 2016, Pope et al.
U.S. Appl. No. 15/684,203, filed Aug. 23, 2017, Pope et al.

\* cited by examiner

BIOMETRIC SENSOR CHIP HAVING DISTRIBUTED SENSOR AND CONTROL CIRCUITRY

CROSS-REFERENCE TO RELATED APPLICATION

This application is a continuation-in-part of U.S. patent application Ser. No. 15/090,474, filed Apr. 4, 2016, entitled "Biometric Sensor Chip Having Distributed Sensor and Control Circuitry," which is a continuation of U.S. patent application Ser. No. 14/294,903, filed Jun. 3, 2014, entitled "Biometric Sensor Chip Having Distributed Sensor and Control Circuitry," which claims the benefit under 35 U.S.C. § 119(e) of U.S. Provisional Patent Application No. 61/831,586, filed Jun. 5, 2013, entitled "Biometric Sensor Chip Having Distributed Sensor and Control Circuitry," the entireties of which are incorporated herein by reference as if fully disclosed herein.

TECHNICAL FIELD

Embodiments described herein relate generally to a sensor, and more particularly to a substrate having a biometric sensor array on a first side that is coupled to control circuitry positioned on a second side of the substrate.

BACKGROUND

Biometric sensing devices are increasingly common in computer or network security applications, financial applications, surveillance applications, and system access control applications. Biometric sensing devices detect or image a unique physical or behavioral trait of a person, providing biometric data that can reliably identify the person. For example, a fingerprint includes a unique pattern of ridges and valleys that can be imaged by a fingerprint sensor. The image of the fingerprint, or the unique characteristics of the fingerprint, is compared to previously captured reference data, such as a reference fingerprint image. The identity of the person is obtained or verified when the newly captured fingerprint image matches the reference fingerprint image Devices that image fingerprints or other biometric data can be incorporated into a variety of electronic devices to provide enhanced functionality for those devices. Generally, many electronic devices, such as smart phones, tablet computing devices, computers, security keypads, and the like, may place a premium on space within the device. That is, the complexity of such devices leads to the incorporation of additional components, circuits and the like when compared with previous generations of devices. In order to maintain a similar form factor and/or size, the volume and/or area occupied by internal components may remain constant or even shrink between generations of electronic devices. Thus, more and more components compete for the same space. Thus, efficient designs of internal components, including biometric sensors, may be both useful and desired.

SUMMARY

Embodiments herein may take the form of a biometric sensor formed on a substrate (e.g., a "chip") in such a fashion that electronic components are distributed across opposing sides of the substrate. One or more through-silicon vias (TSVs) may connect the electronic components on the opposing sides. The TSVs may carry control signals between components, power to one or more components, data between components, and the like. Generally the electronic components may function as if laid out and positioned on a single side of the substrate.

One embodiment described herein takes the form of a sensor that includes a sensor array formed on a first side of a substrate and at least one circuit operative to communicate with the sensor array formed on a second side of the substrate. At least one via extends through the substrate to electrically connect the sensor array to the at least one circuit. Placing the at least one circuit on the second side of the substrate allows the sensor array to occupy substantially all of the first side of the substrate.

In some embodiments, multiple vias extend through the substrate, and each via may underlie one of a plurality of traces forming the sensor array.

In still other embodiments, the multiple vias separate the sensor array into two or more sensor sub-arrays.

In yet other embodiments, each of the two or more sensor sub-arrays is separately addressable by the at least one circuit.

In some embodiments, an electronic device includes a cover glass and a sensor positioned below the cover glass. The sensor includes a sensor array formed on a first side of a substrate; at least one circuit operative to communicate with the sensor array formed on a second opposing side of the substrate; and at least one via extending through the substrate to electrically connect the sensor array to the at least one circuit. The sensor array may occupy substantially all of the first side of the substrate. As one example, the cover glass and sensor are included in a button of the electronic device.

In some embodiments, a method for manufacturing a sensor includes forming one or more vias in a first circuit wafer that includes one or more electrical components, where each via comprises a blind via that extends only partially through a thickness of the first circuit wafer. A first side of a substrate wafer is formed over a first side of the first circuit wafer, where the first side of the first circuit wafer includes openings to the one or more vias in the first circuit wafer. A temporary carrier wafer is attached to a second side of the substrate wafer and the first circuit wafer thinned on a second side of the first circuit wafer to expose the one or more vias in the first circuit wafer. A second circuit wafer is then formed over the second side of the first circuit wafer, where the second circuit wafer includes a sensor array and the one or more vias in the first circuit wafer operably connect the one or more electrical components in the first circuit wafer to the sensor array in the second circuit wafer. An isolator layer can be formed over the second side of the first circuit wafer prior to forming the second circuit wafer over the second side of the first circuit wafer. Back end of line operations may be performed on the substrate wafer prior to attaching the temporary carrier wafer to the second side of the substrate wafer. In some embodiments, the sensor array includes a three metal redistribution layer of a grounding metal layer and two sensing and drive layers. The temporary carrier wafer is removed from the substrate wafer.

DETAILED DESCRIPTION

Generally, embodiments herein may take the form of a biometric sensor formed on a substrate (e.g., a "chip") in such a fashion that electronic components are distributed across opposing sides of the substrate. One or more through-silicon vias (TSVs) may connect the electronic components on the opposing sides. The TSVs may carry control signals between components, power to one or more components, data between components, and the like. Generally, the electronic components may function as if laid out and positioned on a single side of the substrate.

In many embodiments, a sensor array may be deposited on a first side of the substrate. Likewise, control circuitry (such as CMOS circuits) may be positioned on a second, opposing side of the substrate. By separating the control circuitry and the sensor array in this fashion, the area available on the chip to be occupied by the sensor array may be increased in comparison to a same-size chip having both sensor and control circuitry on the same side. Thus, embodiments may make more efficient use of the available area on a chip's surface, and/or may facilitate placing a larger sensor on a chip's surface than may be achieved when both the sensor and control circuitry are positioned on a single side of the substrate.

Figure 1:
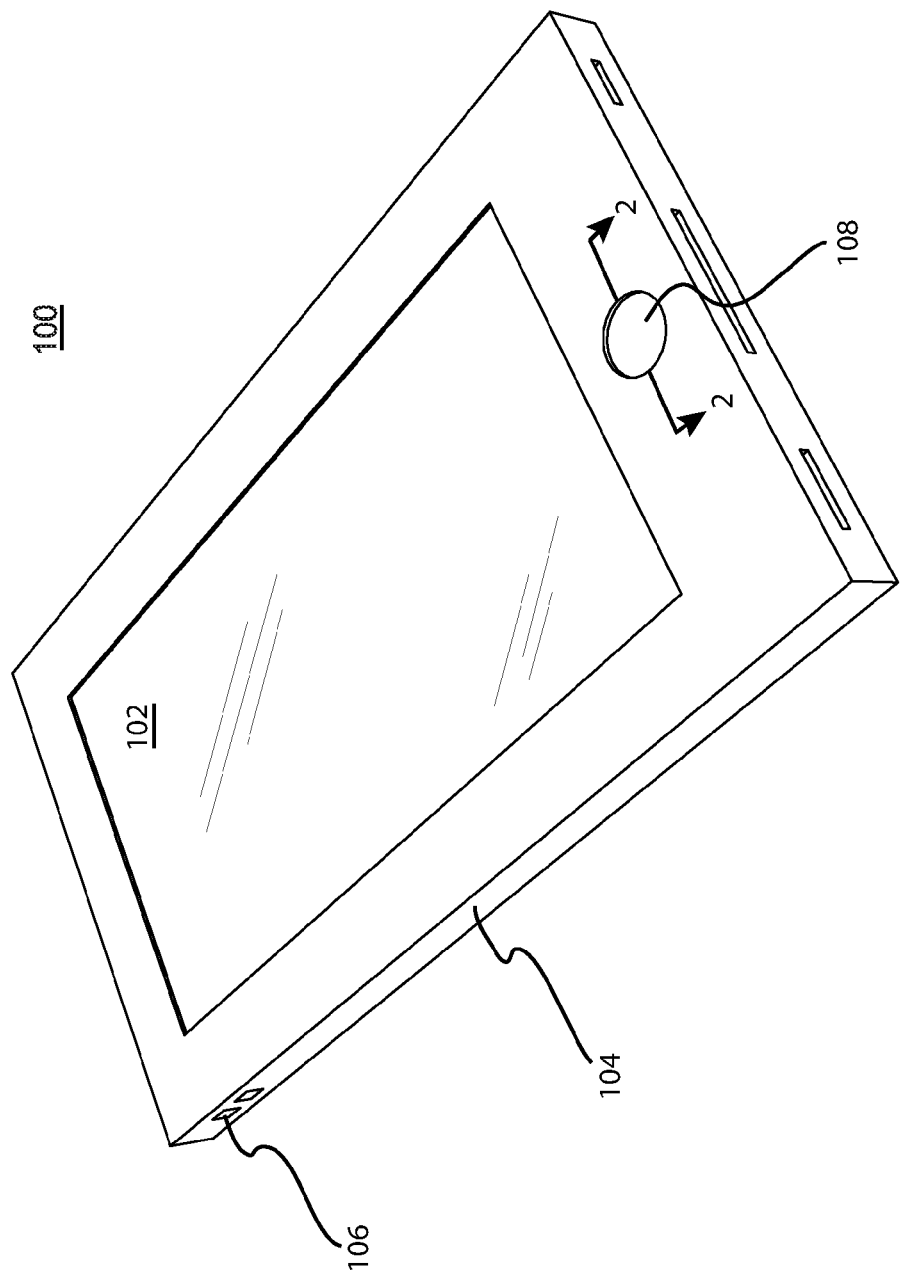
FIG. 1 depicts a sample device in which an example biometric sensor may be incorporated.

Further, the control circuitry may be positioned on the second side of the substrate in such a fashion that the distance between the control circuitry and the sensor may be reduced when compared to biometric sensor packages having both on one side. Essentially, the depth of a TSV connecting the sensor array to the control circuitry may be less than the length of a trace or run that may be required to connect the two when the sensor and circuitry occupy a single side of a chip or other substrate, as discussed in more detail below. Likewise, the control circuitry may be shielded by the substrate from any fringing field effects of the sensor array. FIG. 1 generally depicts a sample electronic device that may incorporate a biometric sensor in accordance with certain embodiments described herein. As can be seen, the electronic device may take the form of a mobile smart phone. Embodiments described herein may also be incorporated into, or used with, a variety of other electronic devices such as tablet computing devices, stand-alone computers, wearable devices, electronics systems for appliances, electronics systems for automobiles, security systems, and the like.

Although reference is made herein to the orientation of particular objects and elements, it should be understood that such orientations may be altered or varied in certain embodiments. Likewise, orientations and directions discussed herein are generally provided with respect to the figures herein. Accordingly, "up," "down," "upper," "lower," "front," "rear," "side" and like terms are intended as relative terms, not absolute.

Referring now to FIG. 1, the biometric sensor may be located beneath any suitable portion of the exterior of the device 100. The biometric sensor may be located beneath a cover glass 102, for example. Likewise, the biometric sensor may be located beneath a sidewall 104 or other portion of the device housing. As yet another option, the biometric sensor may be located beneath an input mechanism 106 of the device 100. One example embodiment includes a biometric sensor located beneath a button 108 of the device.

In embodiments having a biometric sensor located beneath a cover glass or under a portion of a housing (such as sidewall 104), multiple biometric sensors may be tiled or otherwise positioned to extend sensing capability across a larger area of the cover glass/housing.

Similarly, a single biometric sensor may be scaled to underlie a significant portion of either the cover glass 102 or the housing. It should be appreciated that the biometric sensor(s) may be positioned in such a fashion as to not interfere with viewing of a display through the cover glass 102 (if such a display is present). Thus, for example, the biometric sensor(s) may be positioned beneath a display element of the electronic device 100, or sensor may be formed from a relatively optically transparent material such as indium-tin-oxide or other suitable materials.

Figure 2:
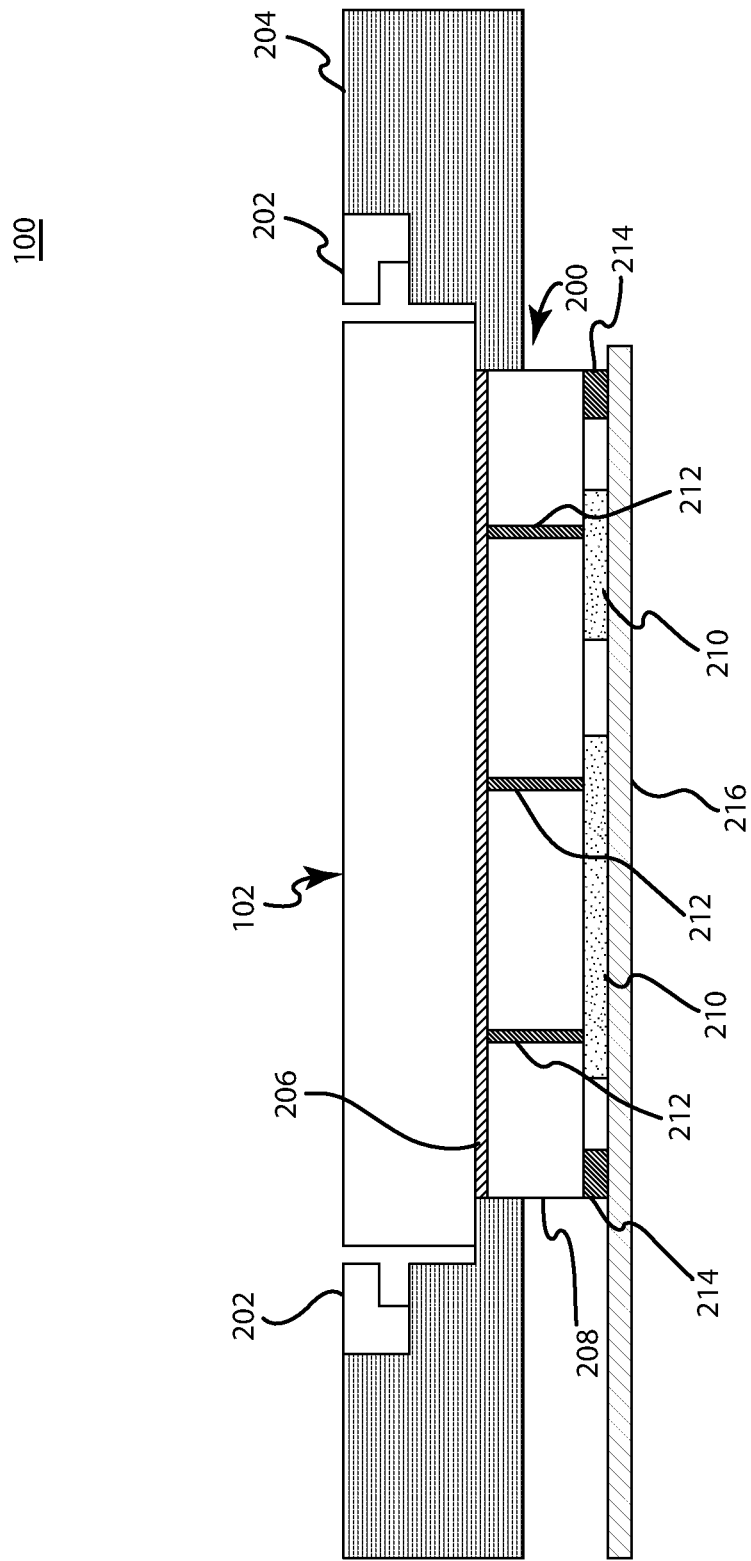
FIG. 2 is a cross-sectional view taken along line 2-2 of FIG. 1, showing a relative position of a biometric sensor chip within the sample device of FIG. 1.

FIG. 2 is a cross-sectional view taken along line 2-2 of FIG. 1, showing an example location of a biometric sensor 200 with respect to the button 108 of the sample electronic device 100. Generally, the sensor is positioned adjacent to the button 108, such that the two touch. It should be appreciated that, in alternate embodiments, the sensor 200 and button 108 may be at least slightly spaced apart from one another. A ground ring 202 may encircle or be positioned adjacent to the button 108. The ground ring may hold a finger or other body portion to be biometrically sensed at a particular voltage with respect to the sensor 200. Although the element is referred to as a "ground ring," the voltage exerted by the element need not be a zero ground voltage. Likewise, the ground ring 202 need not be annular but maybe any suitable shape, which may vary with the shape and/or style of the button 108, the sensor 200, or other portion or dimension of the electronic device 100.

An outer surface 204 of the electronic device 100 may abut the ground ring 202, or otherwise be positioned near the ground ring 202. In embodiments where the ground ring 202 is not present, the outer surface 204 may be proximate the button 108. The outer surface 204 may define a stepped transition or lip that may support the button in some embodiments. Further, in some embodiments, a compliant gel or spring element may be positioned between the lip and the base of the button 108, thereby sealing the interior of the electronic device 100 from the exterior and allowing the button 108 to move upwardly and downwardly, as force is exerted thereon.

In the embodiment shown in FIG. 2, an upper surface of the sensor 200 has a sensor array 206 formed thereon; the sensor array 206 may be positioned proximate to (and in contact with) a lower surface of the button 108. By placing the sensor array nearest the button, the distance at which a finger or other object touching the button is to be scanned or imaged may be minimized. As discussed in more detail below, the sensor array 206 may occupy all or substantially all of the upper surface of the sensor 200. In this arrangement, the ability of the sensor array 206 to image objects atop or adjacent the top of the button 108 may be maximized, since the area occupied by the sensor array on the sensor chip 200 is maximized.

As shown in the cross-sectional view of FIG. 2 and discussed in more detail below, one or more through-silicon vias (TSVs) 212 may extend through the substrate 208 of the sensor 200. The TSVs 212 may generally electrically couple the sensor array 206 to certain circuitry 210 disposed on an opposing side of the substrate 208. For example, CMOS control circuitry 210 may be positioned on a bottom side of the biometric sensor 200 and connected to the sensor array 206 by the TSVs 212. Control and/or data signals may be transmitted between the array and the circuitry through the TSVs. The TSVs 212 may be filled with an electrically conductive material, such as copper or silver, or any other suitable conductor.

Still with reference to FIG. 2, the sensor 200 may be electrically connected to a flex circuit 216 in order to transmit signals to and/or from other portions of the electronic device 100. The flex circuit 216 may route signals between the sensor 200 and a remote processor, for example. In order to facilitate electrical communication, one or more electrical connection surfaces 214 may be formed on the bottom surface of the sensor substrate 208. The exact location of these connection surfaces 214 may vary between embodiments. The connection surfaces may take the form of wire bond pads, bumps or raised surfaces, or any other suitable connector.

Figure 3:
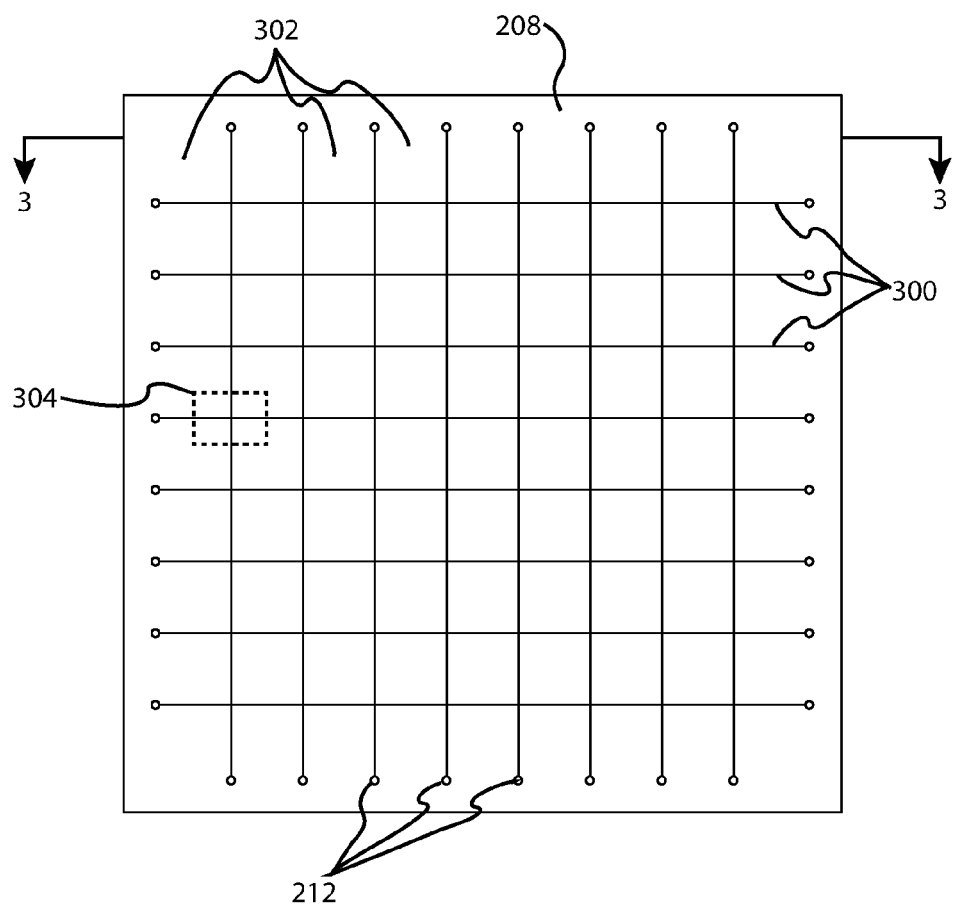
FIG. 3 is a top plan view of an example biometric sensor.

Referring now to FIG. 3, there is shown a top plan view of an example biometric sensor 200. The sensor array 206 may be defined by a set of intersecting rows 300 and columns 302 lines, each of which are formed from electrical traces. Generally, either the row lines 300 or the column lines 302 function as drive lines while the other functions as sense lines. The intersection of each drive line and sense line may define a capacitive sensor element 304 that functions to image a biometric feature of a user's body part that is in contact with, or above, the button 108. The operation of such a capacitive sensor element is generally understood and is therefore not described in detail herein.

The capacitive sensor array may be used, for example, as a fingerprint sensor to image the ridges and valleys of a human finger. In alternative embodiments, the capacitive sensor array may be used as a touch or force sensor.

As shown in FIG. 3, the ends of each row line and column line 300, 302 terminate in a TSV 212. As discussed above, the TSVs 212 may electrically connect the row and column lines (and thus the capacitive sensor elements defined by their intersections) with circuitry 210 disposed on an opposing side of the substrate 208.

Figure 4:
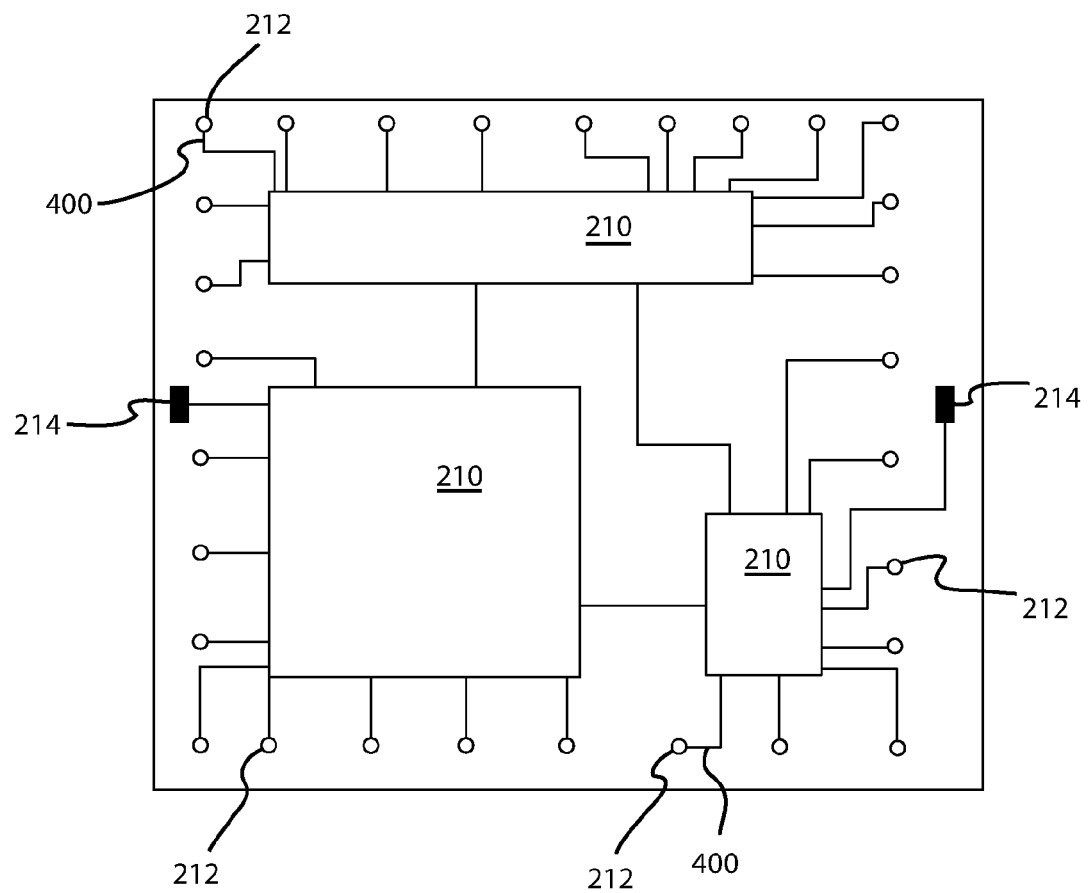
FIG. 4 is a bottom plan view of the example biometric sensor of FIG. 3.

FIG. 4 is a bottom plan view or bottom surface of the example biometric sensor 200 of FIG. 3. In particular, an example disposition of circuitry 210 is depicted. As shown in the figure, traces 400 may connect one or more circuits 210, such as CMOS circuits, to one or more TSVs 212 which, in turn, electrically couple to the sensor array 206 on the top surface of the substrate 208. By placing the circuitry 210 on a different surface of the substrate 208 than the one occupied by the sensor array 206, the array may occupy surface space that would otherwise be dedicated to hosting the circuitry. Thus, a larger imaging area may be provided in a space on a substrate than otherwise achieved if both array and circuitry share a common surface.

Additionally, in many embodiments the overall length of an electrical connection between the sensor array 206 and associated circuitry 210 may be reduced, insofar as the depth of the TSVs 212 may be less than the length of a circuit trace that would connect the sensor array and circuitry if both occupied the same side of the substrate 208. This may both simplify the layout, and speed operation, of the sensor 200.

In addition, the substrate 208 itself may act as a dielectric, shielding the circuitry 210 from any fringe field effects of the sensor array (and vice versa). Thus, certain embodiments may essentially provide electrical shielding to the sensor without introducing any additional layers or materials, such as a ground plane.

Further, insofar as the connection surfaces 214 are generally closer to the flex circuit 216 (as shown in FIG. 2), the sensor may be better integrated with the flex circuit and the rest of the electronic device 100. The connection surfaces 214 need not extend off the sides of the substrate 208, for example, and thus potentially may not obstruct any portion of an adjacent display or the like.

The use of TSVs 212 also obviates the need to wire bond the front surface of the biometric sensor 200 to the flex circuit 216, thereby potentially eliminating the need to edge trench the substrate 208 or otherwise provide a path for an external conductive wire from the biometric sensor's front surface to the flex circuit 216 located beneath the biometric sensor. This may further free up space inside the electronic device 100 that would otherwise be used to route the conductor, and may also increase the area available on the substrate 208 for use by the biometric sensor array insofar as no edge trench need be defined.

Figure 5:
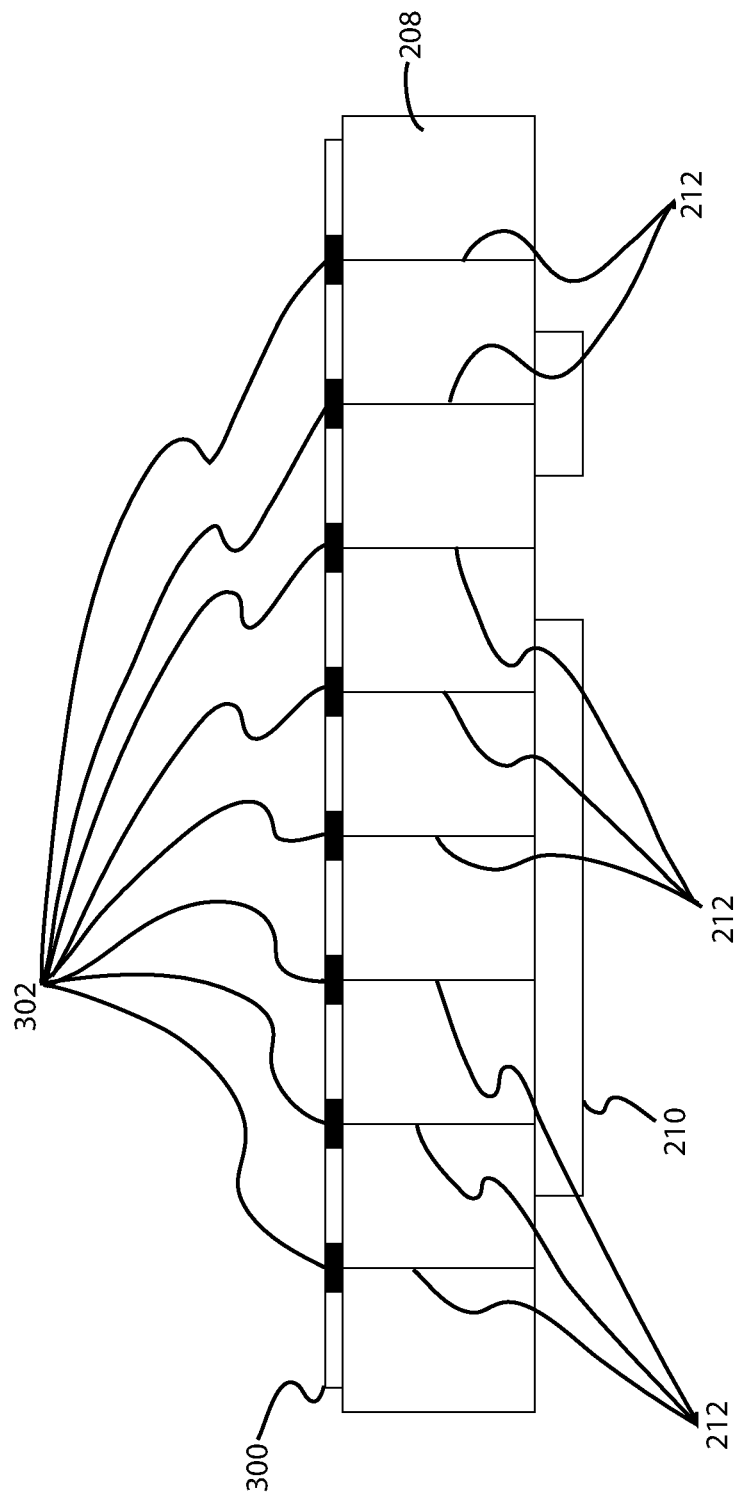
FIG. 5 is a cross-sectional view of the example biometric sensor of FIGS. 3-4, taken along line 5-5 of FIG. 3.

Referring now to FIG. 5, there is shown a cross-sectional view of the example biometric sensor 200 of FIGS. 3-4, taken along line 5-5 in FIG. 3. As shown to best effect in this figure, the TSVs 212 may be routed between the upper sensor array 206 and the lower circuitry 210. Generally, the thickness of the substrate 208 is on the order of 100 microns or less, thereby creating a relatively short electrical routing between the two surfaces.

Figure 6:
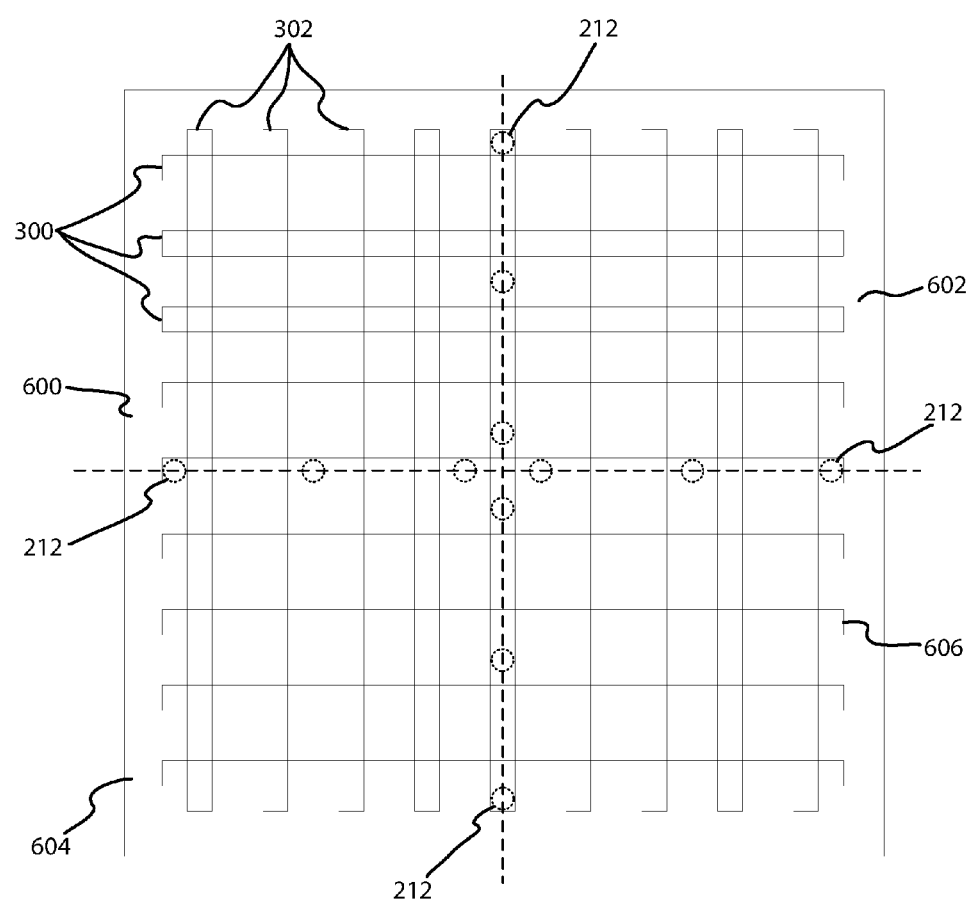
FIG. 6 is a top plan view of an example biometric sensor showing a sample layout of multiple through-silicon vias.

FIG. 6 is a top plan view of an example biometric sensor showing a sample layout of multiple through-silicon vias (TSVs) 212. The TSVs 212 are shown for clarity in this figure, although it should be appreciated that in many embodiments, the TSVs 212 may be concealed from external view by the traces 300, 302 forming the intersecting sets of row and column lines. That is, the diameter of any given TSV 212 may be less than the width of an electrical trace 300, 302. As one example, a TSV may have approximately a 12 micron diameter and a trace may have approximately a 25 micron width. Thus, a TSV 212 may connect a row trace or a column trace to associated circuitry 210 (not shown) on the opposing side of the substrate 208, as generally previously described.

By placing the TSVs 212 beneath the traces 300, 302, the sensor array 206 may effectively be partitioned into multiple sub-arrays. For example, in the embodiment of FIG. 6, the TSVs partition the sensor array 206 into four separate sensor sub-arrays 600, 602, 604, 606, denoted by the dashed lines in FIG. 6.

Essentially, each sub-array 600, 602, 604, 606 may be addressed by, and treated as a separate sensor array by the control circuitry 210 or other circuitry. By partitioning the sensor array 206 in this fashion, it is possibly to drive and/or read only a portion of the drive and sense lines of the array at any given time. This, in turn, may increase the operating speed of the sensor, insofar as: a) some embodiments may permit simultaneous operation of multiple sub-arrays 600, 602, 604, 606; and b) the RC constant for any given combination of drive and sense lines is lower for a sub-array 600, 602, 604, 606 than for any corresponding configuration of drive and sense lines of the entire array 206. Because the drive and sense lines 300, 302 are reduced in length in the sub-array configurations, the effective resistance of each trace is lowered. Thus, the capacitive sensing elements 304 may discharge more quickly, which provides faster biometric imaging by the biometric sensor 200. Resistance may be lowered in this manner because control signals may be transmitted through the TSVs 212 at points within the sensor array, instead of only having control signals carried to the edges of the sensor array as in many conventional sensors.

It should be appreciated that the TSVs 212 need not be spaced evenly, as shown in FIG. 6, but may be positioned as desired under the traces of the sensor array 206. In some embodiments, the TSVs may be formed in such a manner that they are symmetric about one or both of an X and Y axis of the sensor array 206.

In addition, the substrate 208 of the biometric sensor 200 may act as a shield, thereby preventing electrical disturbances from impacting the operation of the sense and/or drive lines. The separation of the sensor array 206 and circuitry 210, as accomplished by the use of TSVs 212, enables the substrate 208 to function in this fashion.

Figure 7A:
FIGS. 7A-7I illustrate a process flow diagram depicting one series of operations for making a sample biometric sensor.
Figure 7B:
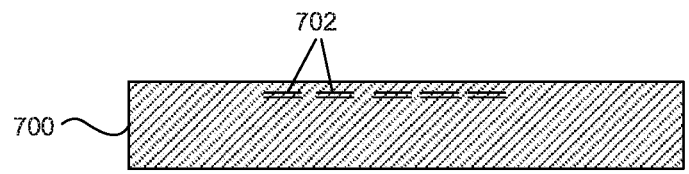
Figure 7C:
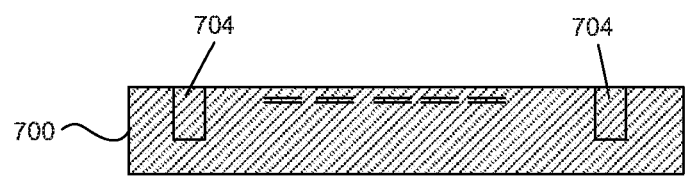
Figure 7D:
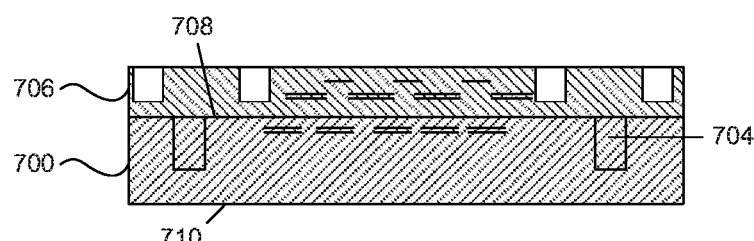
Figure 7E:
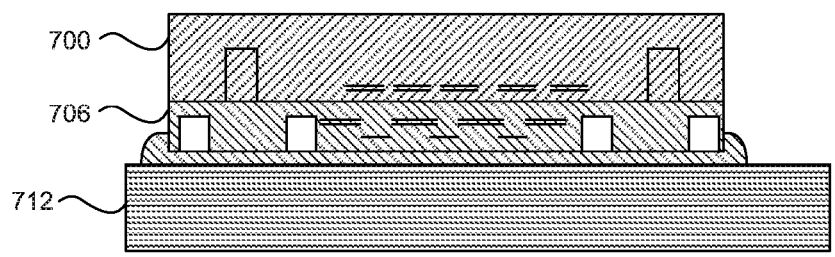
Figure 7F:
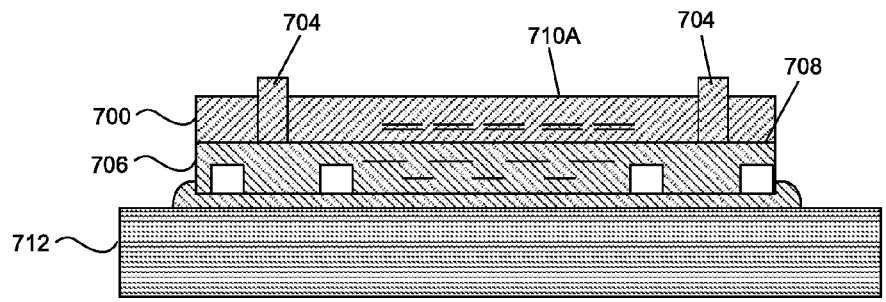
Figure 7G:
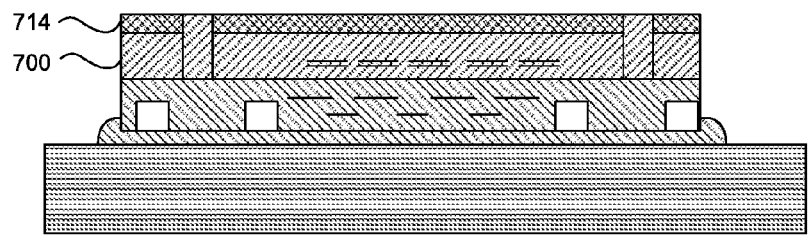
Figure 7H:
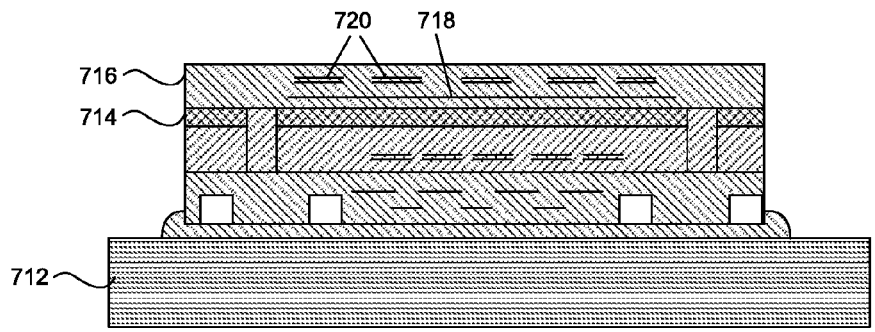
Figure 7I:
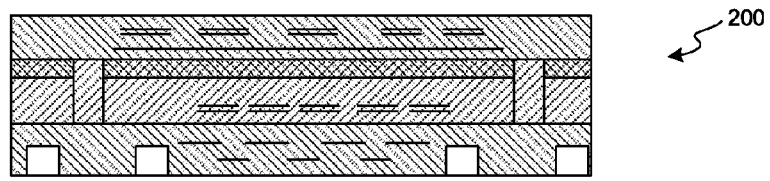
Figure 8:
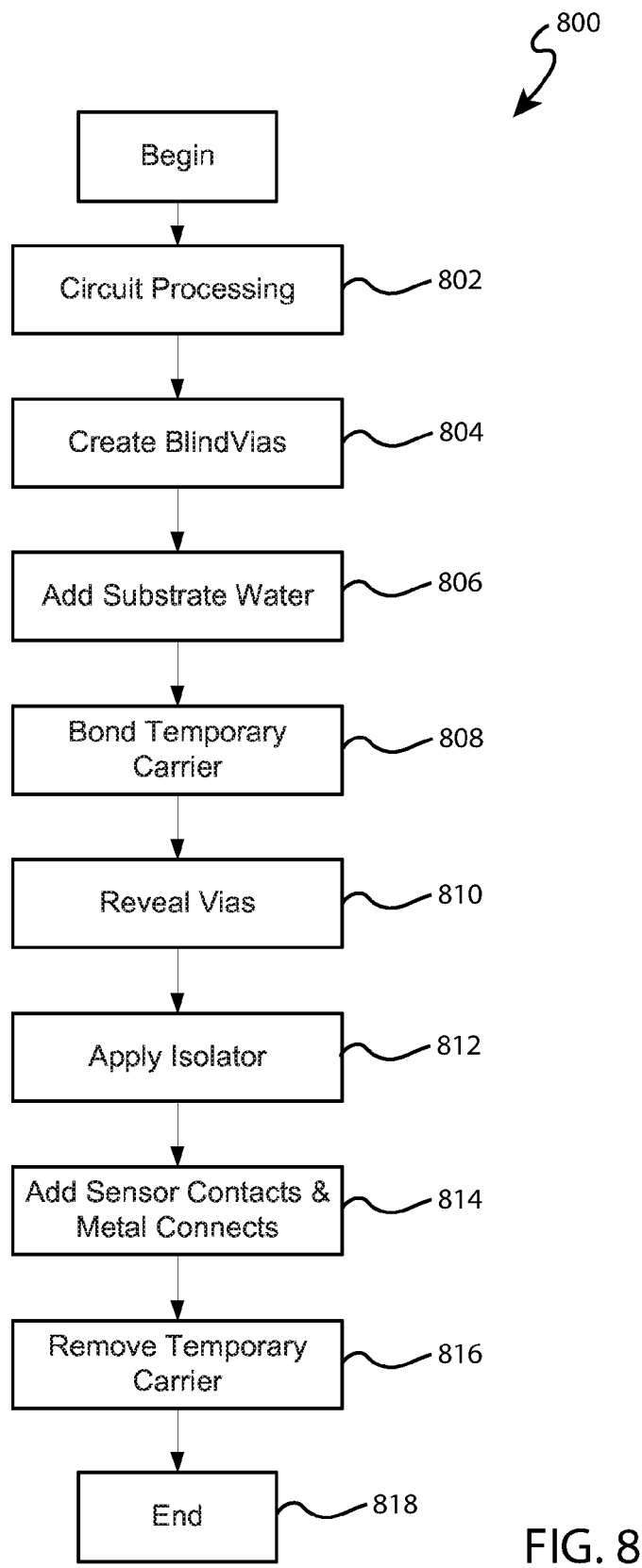
FIG. 8 is a flowchart corresponding to the process flow diagram of FIGS. 7A-7I.

An illustrative method of manufacturing the sensor chip will now be discussed in more detail. FIGS. 7A-7I illustrate a process flow diagram depicting one series of operations for making a sample biometric sensor. FIG. 8 is a flowchart corresponding to the process flow diagram of FIGS. 7A-7I. With reference initially to FIG. 7A, the sensor chip manufacturing process typically begins with a circuit wafer 700. In many instances, the circuit wafer 700 may be silicon. With reference to FIG. 8, once a circuit wafer is provided or created, the method 800 may begin with operation 802 and the circuitry and other components may be added or otherwise defined in the circuit wafer. For example, front end of line (FEOL) CMOS processing can be used to add individual devices, e.g., transistors, capacitors, resistors, and the like, to the circuit wafer. In this example, one or more interconnects, such as metal interconnect layers, may also be added to the circuit wafer. As shown in FIG. 7B, after operation 802, the circuit wafer includes a plurality of electrical components and/or traces 702 defined thereon.

After operation 802, the method 800 may proceed to operation 804. With reference to FIGS. 7C and 8, in operation 804, one or more vias 704 are defined within the circuit wafer 700. The via(s) may be defined through etching, grinding, chemical deposition, or the like. Depending on the thickness of the circuit wafer the one or more vias may be blind vias and may not extend through the entire thickness of the circuit wafer 700 during operation 804. For example, the circuit wafer 700 may be sufficiently thin that extending the vias 704 through the entire thickness of the circuit wafer could cause the circuit wafer to crack or otherwise hinder additional processing. In these embodiments, the vias 704 terminate prior to the opposite edge of the circuit wafer 700. Accordingly, as shown in FIG. 7C, the vias 704 extend only three-quarters through the thickness of the circuit wafer 700.

With reference again to FIG. 8, after the vias are defined through the circuit wafer, the method 800 may proceed to operation 806. In operation 806, a substrate wafer is added to the circuit wafer. With reference to FIG. 7D, in operation 806, the substrate wafer 706 is bonded to the circuit wafer 700 and then back end of line (BEOL) operations may be performed. For example, contacts (e.g., bond pads), interconnect wires, and/or dielectric structures may be added to the circuit wafer during operation 806. Generally, the BEOL processing and substrate wafer will be added to the side 708 of the circuit wafer 700 that has an opening for the vias 704. In other words, the face of the circuit wafer 700 including the openings to the vias 704 is bonded to the substrate wafer 706 and the face 710 without via openings is unbounded.

With reference again to FIG. 8, after operation 806, the method 800 may proceed to operation 808. In operation 808, a temporary carrier wafer is bonded to the substrate wafer or the other structures formed during BEOL processing. With reference to FIG. 7E, the temporary carrier wafer 712 may be bonded to the substrate wafer 706. The temporary carrier wafer 712 can be bonded to the substrate wafer 706 using a number of different techniques, such as, but not limited to, direct bonding, plasma activated bonding, eutectic bonding, and/or hybrid bonding.

Once the temporary carrier wafer 712 has been bonded to the substrate wafer 706, the method 800 may proceed to operation 810. In operation 810, the circuit wafer is thinned to reveal the vias. With reference to FIG. 7F, the circuit wafer 700 is thinned to reduce the thickness such that the vias 704 now extend through the entire thickness of the circuit wafer 700. The circuit wafer may be thinned in a number of different manners, such as, but not limited to, grinding, polishing, and selective etching processes. Because the side 708 of the circuit wafer 700 with the via openings is bonded to the substrate wafer 706, the grinding or other thinning process is done to the un-bonded or un-processed side 710A of the circuit wafer 700 and removes the excess material between the terminal end of the vias, such that the vias 704 can be exposed.

After operation 810, the method 800 may proceed to operation 812. In operation 812, an isolator may be applied to the circuit wafer. With reference to FIG. 7G a dielectric or other isolation layer 714 is applied to the top of the circuit wafer 700. Once the isolator layer 714 is applied, the method 800 may proceed to operation 814. In operation 814, one or more metal and/or sensor contacts, such as the sense and drive lines, are added to or over the isolator layer. With reference to FIG. 7H, one or more layers of metal or other connection elements are added to a circuit wafer 716. For example, a three metal redistribution layer (RDL) which may include a grounding metal layer 718 and two sensing/drive layers 720 for the biometric sensor may be added to the circuit wafer 716 in operation 814.

With reference again to FIG. 8, after the sensor contacts and metal contacts have been added, the method 800 may proceed to operation 816. In operation 816, the temporary carrier wafer may be removed. With reference to FIG. 7I, the temporary carrier wafer 712 may be de-bonded or otherwise removed. For example, the temporary carrier wafer may be a polymer material that may be removed using one or more solvents. As another example, the temporary carrier wafer may be removed through grinding, polishing, or the like.

After the temporary carrier wafer has been removed, the method 800 may proceed to an end state 818. The example biometric sensor 200 is shown in FIG. 7I.

Although embodiments have been described herein with respect to particular sensor types, configurations and methods of manufacture, it should be appreciated that alternative embodiments may vary one or more of these. For example, certain capacitive sensors, such as touch sensors and/or force sensors, may employ distribution of sensor arrays and circuitry across differing surfaces of a substrate as described herein, including connection of the same with TSVs. Likewise, certain embodiments may omit elements described herein, vary the order of operations with respect to methods described herein, and the like.

The present disclosure recognizes that personal information data, including biometric data, in the present technology, can be used to the benefit of users. For example, the use of biometric authentication data can be used for convenient access to device features without the use of passwords. In other examples, user biometric data is collected for providing users with feedback about their health or fitness levels. Further, other uses for personal information data, including biometric data, that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure, including the use of data encryption and security methods that meets or exceeds industry or government standards. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data, including biometric data. That is, the present disclosure contemplates that hardware and/or software elements can be provided to prevent or block access to such personal information data. For example, in the case of biometric authentication methods, the present technology can be configured to allow users to optionally bypass biometric authentication steps by providing secure information such as passwords, personal identification numbers (PINS), touch gestures, or other authentication methods, alone or in combination, known to those of skill in the art. In another example, users can select to remove, disable, or restrict access to certain health-related applications collecting users' personal health or fitness data.

We claim:

1. A biometric sensor, comprising:
   a capacitive sensor array configured to image biometric data and formed on a first side of a substrate, the sensor array comprising:
      a first plurality of electrical traces defining a plurality of rows;
      a second plurality of electrical traces defining a plurality of columns, the plurality of columns intersecting the plurality of rows, thereby defining a plurality of intersections; and
      a capacitive sensing element formed at each of the plurality of intersections;
   at least one circuit formed on a second opposing side of the substrate and configured to communicate with the sensor array; and
   a plurality of vias extending through the substrate to electrically connect the sensor array to the at least one circuit; wherein
   each of the plurality of vias underlies an electrical trace chosen from the first or the second plurality of electrical traces.

2. The biometric sensor of claim 1, wherein the plurality of vias separates the sensor array into a plurality of sensor sub-arrays.

3. The biometric sensor of claim 2, wherein each sensor sub-array in the plurality of sensor sub-arrays is separately addressable by the at least one circuit.

4. The biometric sensor of claim 2, wherein at least one of the plurality of sensor sub-arrays comprises:
   a subgroup of the plurality of rows; and
   a subgroup of the plurality of columns, the subgroup of the plurality of columns intersecting the subgroup of the plurality of rows;
   wherein an RC constant of the at least one of the plurality of sensor sub-arrays is less than an RC constant of the sensor array.

5. The biometric sensor of claim 2, wherein the plurality of sub-arrays images a biometric parameter faster than the sensor array.

6. The biometric sensor of claim 1, wherein the substrate electrically shields the at least one circuit from the capacitive sensor array.

7. A fingerprint sensor, comprising:
   a sensor array comprising biometric sensing elements formed on a first side of a substrate, the sensor array comprising:
      a first plurality of electrical traces defining a plurality of rows; and
      a second plurality of electrical traces defining a plurality of columns, the plurality of columns intersecting the plurality of rows to define a plurality of intersections;
      wherein a respective biometric sensing element is formed at each of the plurality of intersections and each biometric sensing element is configured to image a fingerprint;
   at least one circuit formed on a second opposing side of the substrate and configured to communicate with the sensor array; and
   a plurality of vias extending through the substrate to electrically connect the sensor array to the at least one circuit, wherein each of the plurality of vias is formed at a unique end of one of the plurality of rows and the plurality of columns.

8. The fingerprint sensor of claim 7, wherein the substrate electrically shields the at least one circuit from the sensor array.

9. A fingerprint sensor, comprising:
   a sensor array configured to capture fingerprint data and formed on a first side of a substrate, the sensor array comprising:
      a first plurality of electrical traces defining a plurality of rows; and
      a second plurality of electrical traces defining a plurality of columns, the plurality of columns intersecting the plurality of rows, thereby defining a plurality of intersections; and
      a capacitive sensing element formed at each of the plurality of intersections;
   at least one circuit formed on a second opposing side of the substrate and operative to communicate with the sensor array; and
   a plurality of vias extending through the substrate to electrically connect the sensor array to the at least one circuit, wherein each of the plurality of vias underlies a trace chosen from the first or second plurality of traces.

10. The fingerprint sensor of claim 9, wherein the plurality of vias separates the sensor array into a plurality of sensor sub-arrays.

11. The fingerprint sensor of claim 10, wherein each sensor sub-array in the plurality of sensor sub-arrays is separately addressable by the at least one circuit.

12. The fingerprint sensor of claim 10, wherein at least one of the plurality of sensor sub-arrays comprises:
a subgroup of the plurality of rows; and
a subgroup of the plurality of columns, the subgroup of the plurality of columns intersecting the subgroup of the plurality of rows;
wherein an RC constant of the at least one of the plurality of sensor sub-arrays is less than an RC constant of the sensor array.

13. The fingerprint sensor of claim 10, wherein the plurality of sub-arrays images a biometric parameter faster than the sensor array.

14. The fingerprint sensor of claim 9, wherein the substrate electrically shields the at least one circuit from the sensor array.

15. An electronic device, comprising:
a cover layer; and
a fingerprint sensor positioned below the cover layer, the fingerprint sensor comprising:
a sensor array configured to image fingerprint data and formed on a first side of a substrate, the sensor array comprising:
a first plurality of electrical traces defining a plurality of rows;
a second plurality of electrical traces defining a plurality of columns, the plurality of columns intersecting the plurality of rows to define a plurality of intersections; and
a capacitive sensing element formed at each of the plurality of intersections;
at least one circuit formed on a second opposing side of the substrate and operative to communicate with the sensor array; and
a plurality of vias extending through the substrate to electrically connect the sensor array to the at least one circuit; wherein
each of the plurality of vias underlies an electrical trace chosen from the first or the second plurality of electrical traces; or
each of the plurality of vias is formed at a unique end of one of the plurality of rows and the plurality of columns.

16. The electronic device of claim 15, wherein the substrate electrically shields the at least one circuit from the sensor array.

* * * * *